United States Patent
Gho

(10) Patent No.: US 6,579,540 B1
(45) Date of Patent: *Jun. 17, 2003

(54) USE OF PHYSIOLOGICALLY ACCEPTABLE VANADIUM COMPOUNDS, SALTS AND COMPLEXES

(75) Inventor: Conradus Ghosal Gho, Bunde (NL)

(73) Assignee: Gho'st Holding B.V., Bunde (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/463,697

(22) PCT Filed: Jul. 29, 1998

(86) PCT No.: PCT/NL98/00431

§ 371 (c)(1), (2), (4) Date: Mar. 17, 2000

(87) PCT Pub. No.: WO96/23811

PCT Pub. Date: Aug. 8, 1996

(30) Foreign Application Priority Data

Jul. 29, 1997 (NL) .............................. 1006681

(51) Int. Cl.⁷ .............................. A61K 33/26
(52) U.S. Cl. ...................................... 424/646
(58) Field of Search ......................... 424/646

(56) References Cited

U.S. PATENT DOCUMENTS 5,583,242 A    12/1996    Schieven .................... 556/44

FOREIGN PATENT DOCUMENTS

WO    WO 90/12563    11/1990

OTHER PUBLICATIONS

Saunders Manual of Medical Practice p. 279, 1994.*
Webb A.R. "The role of the oesophageal Doppler in the prevention of postoperative complications" International Journal of Intensive Care, 1997 4/3 (96–104). ISSN: 1350–2794.*

* cited by examiner

Primary Examiner—Theodore J. Criares
Assistant Examiner—Jennifer Kim
(74) Attorney, Agent, or Firm—Sughrue Mion, PLLC

(57) ABSTRACT

Use of a physiologically acceptable vanadium compound, salt or complex as active component in the preparation of a pharmaceutical composition for the prophylactic treatment of secondary injury of tissue, said secondary injury being induced by primary injury of mainly surrounding tissue, in particular surrounding tissue, and being the result of a traumatic event.

4 Claims, 2 Drawing Sheets

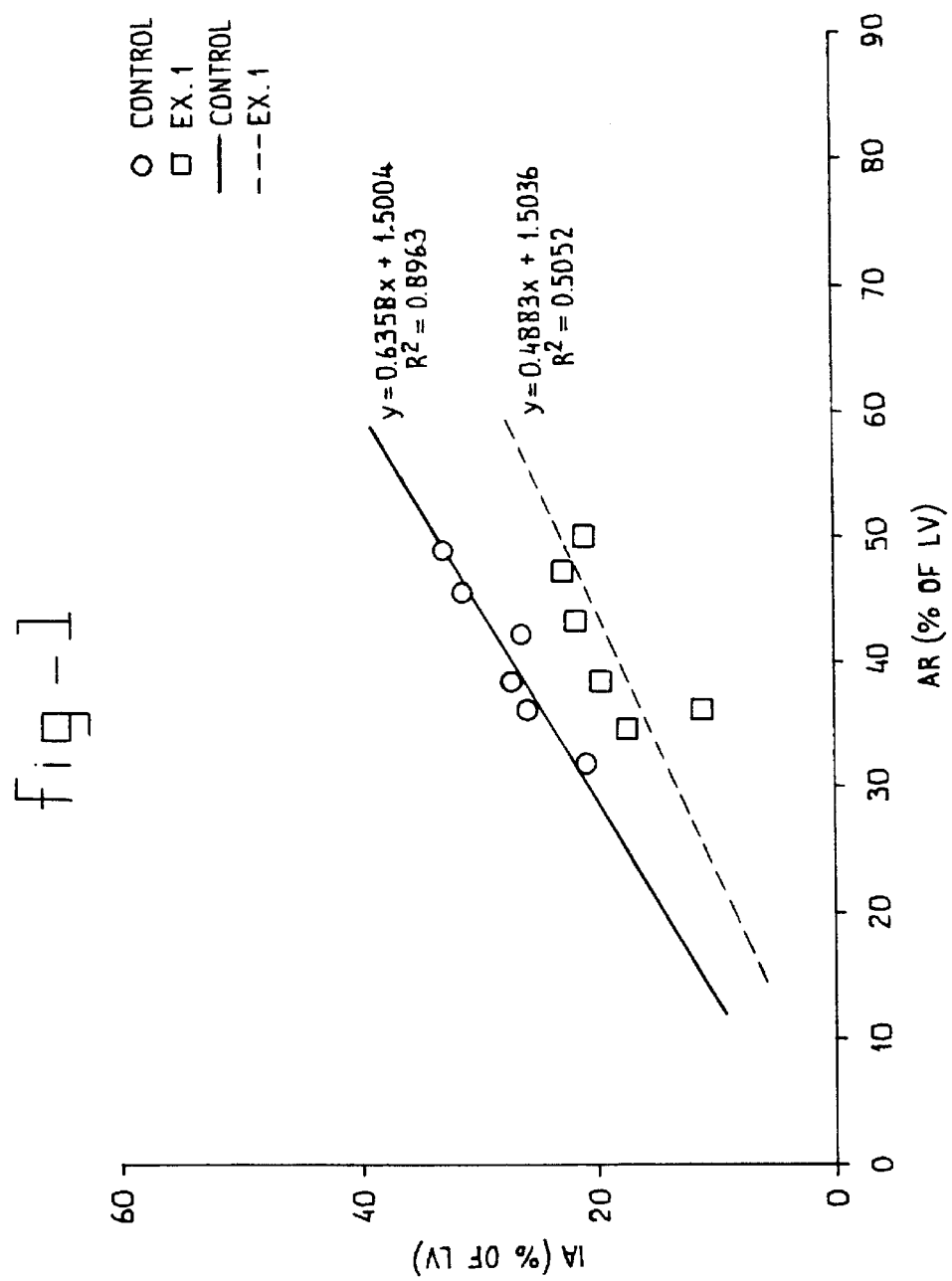

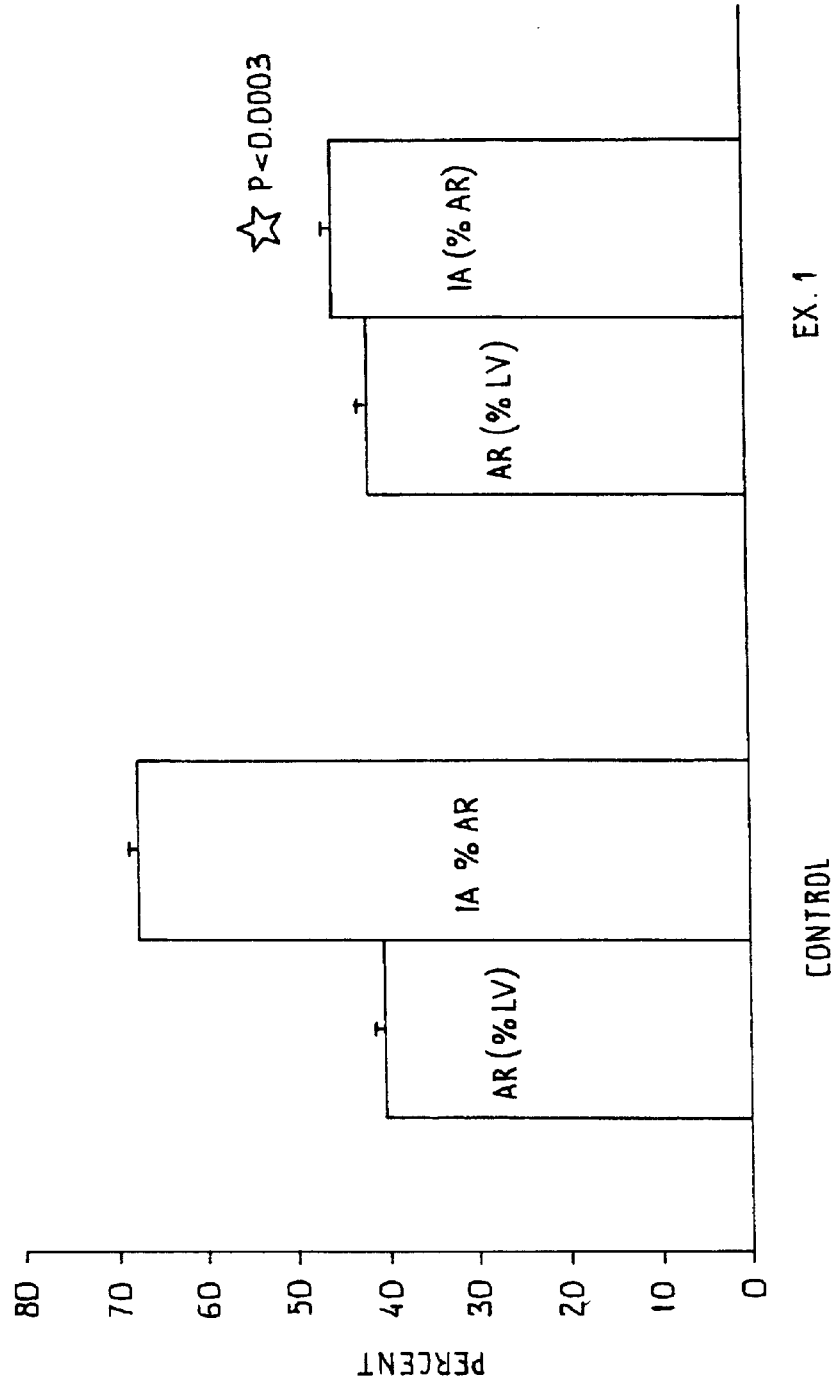

USE OF PHYSIOLOGICALLY ACCEPTABLE VANADIUM COMPOUNDS, SALTS AND COMPLEXES

The present invention relates to a novel therapeutical use of physiologically acceptable vanadium compounds, salts or complexes. The present invention relates in particular to the use of a physiologically acceptable vanadium compound, salt or complex as active component in the preparation of a pharmaceutical composition for the prophylactic treatment of secondary injury of tissue, said secondary injury being induced by primary injury of mainly surrounding tissue, in particular surrounding tissue, and being the result of a traumatic event. It will be clear to the person skilled in the art that secondary injury of tissue may also occur by toxins secreted by already injured tissue and that said already injured tissue has not necessarily to be located in the direct vicinity of the tissue to be protected from secondary injury. In this description the terms vanadium compound, salt or complex are used interchangeably and refer to an organic, inorganic or organometallic compound containing at least one vanadium atom and/or ion in the usual oxidation states, preferably V(II), V(III), V(IV) and/or V(V), said compound optionally being a cation or an anion and optionally being a component of an ion pair.

The use of vanadium compounds for therapeutic purposes is known. For instance, WO 90/12563 discloses the therapeutic use of compositions comprising vanadium compounds as active substance for healing mammalian tissue, e.g. the skin and organs such as heart and brain, wherein vanadium compounds are repeatedly administered in a selected concentration range over a prolonged period of time. In particular, these compositions are said to be able to prevent wrinkles in skin tissue.

The mechanism by which the vanadium compounds according to WO 90/12563 act is not clear as they may inhibit degenerative processes—reduced rate of cell death—and/or stimulate regenerative processes—increased rate of cell proliferation—wherein the net effect is that cell growth surpasses cell death which ultimately leads to healing of the injured tissue. It is, however, disclosed that the vanadium compounds have a stimulating effect on cell proliferation by inhibiting enzymatic dephosphorylation whereby growth factors such as epidermal growth factor (EGF), insulin and platelet-derived growth factor are active for a prolonged period. It is furthermore suggested that the vanadium compounds would promote the healing of e.g. heart and brain. As however heart and brain are non-proliferative tissue the suggested treatment would be unsuccessful on the basis of the postulated mechanism as set out in said cited document and a person skilled in the art would not contemplate treatment of such tissue with vanadium compounds on the basis of the cited disclosure. In this context non-proliferative tissue is understood as tissue or cells which under normal circumstances hardly proliferate. More particularly, non-proliferative tissue is only able to differentiate and thus direct or primary injury of said non-proliferative tissue, e.g. liver necrosis, can therefore not be healed by the use of a vanadium compound said to stimulate the process of proliferation. For example, the mitotoxic index of liver cells as example of non-proliferative tissue under normal conditions is extremely low and is about 1:10.000 to 1:20.000. No evidence for the promoting effect of vanadium compounds on the healing of heart or brain tissue is presented and, consequently, WO 90/12563 is considered as only disclosing the use of vanadium compounds for the enhancement of cell proliferation which in fact can only be effective in so far proliferative tissue, e.g. the skin, is involved, thereby healing direct or primary injury of said proliferative tissue. No disclosure of treatment of non-proliferative tissue is taught.

Besides the growth factor and insulin mimicking properties of vanadium compounds being known the compounds are further known to be Na/K ATP-ase inhibitors, free radical scavengers, in particular superoxide radical scavengers produced by xanthine-oxidase in injured tissues, e.g. ischaemic tissue, burns and other traumata, and inhibitors of the angiotensin II type 2 receptor.

Superoxide radicals can induce apoptosis in tissue and vanadium compounds are therefore expected to be apoptosis inhibitors by scavenging the superoxide radicals. Additionally, Yamada et al. [T. Yamada, M. Horiuchi and V. J. Dzau, Procl. Natl. Acad. Sci. U.S.A 93, 156–160 (1996)] disclose that the angiotensin II type 2 receptor mediates apoptosis. Said receptor is abundantly present in fetal tissue and immature brain and mediates anti-growth effects on vascular smooth tissue and endothelial tissue, wherein the cellular mechanism appears to involve enhancement of the dephosphorylation of mitogen-activated protein kinase (MAP kinase). It should be understood that in the present description immature brain tissue is considered as proliferative tissue. From in vitro studies they conclude that vanadate attenuated the dephosphorylation of MAP kinases thereby inhibiting the angiotensin II type 2 receptor and preventing apoptosis. Thus the suggestion of apoptosis inhibition in these types of tissue by application of vanadium compounds is provided. No data of such application is, however, provided in vitro or in vivo and no non-proliferative tissue is mentioned.

Buerke et al. [M. Buerke, T. Murohara, C. Skurk, C. Nuss, K. Tomaselli and A. M. Lefer, Proc. Natl. Acad. Sci. U.S.A. 92, 8031–8035 (1995)] disclose the use of insulin-like growth factor (IGF) for preventing reperfusion injury after ischaemia. From in vitro studies they conclude that IGF prevents myocardial injury after reperfusion and that pretreatment with IGF affords cardioprotection. Several mechanisms are present to elucidate these effects of IGF including neutrophil accumulation in the ischaemic-reperfused myocardium, inhibition of polymorphonuclear leucocyte-induced cardiac necrosis and induction of reperfusion induced apoptosis of cardiac myocites. However, stimulation of IGF in vivo to reduce reperfusion damage, i.e. indirect or secondary injury of the myocardium, is not disclosed. In addition, Buerke et al. used IGF intracoronary as it would decompose within a very short period of time if it would be administered intravenously. Furthermore, isolated growth factors such as IGF-I, IGF-II and EGF can be obtained in usable quantities only by recombinant technology and are therefore extremely expensive. Use thereof in medicine is therefore also possible only on a very limited scale.

Olivetti et al. [G. Olivetti, R. Abbi, F. Quaini, J. Kajstura, W. Cheng, J. A. Nitahara, E. Quaini, C. DiLoreto, C. A. Beltrami, S. Krajewski, J. C. Reed and P. Anversa, N. Engl. J. Med. 16, 1131–1141 (1997)] disclose that death of myocyte cells as a result of ischaemia occurs through apoptosis and necrosis. Nothing is suggested or disclosed about indirect or secondary injury caused by reperfusion after ischaemia. Nothing is mentioned concerning treatment of any kind. Nothing is disclosed about vanadium compounds.

U.S. Pat. No. 5,583,242 discloses the use of vanadium compounds to inhibit malignant B lymphocyte proliferation by inducing apoptosis in such cells. This effect could, however, not be observed in human T cell leukaemia cell lines or in human colon carcinoma cells thereby indicating that vanadium compounds cannot induce apoptosis in all kinds of cells. Nothing is mentioned about other cell types. As no correlation between B cell population and injury of heart or epithelial tissue is known and B cell population does not increase in events of injury of myocardial or epithelial tissue, application of vanadium compounds for treatment of myocardial or epithelial tissue is not suggested by this document.

Furthermore, vanadium compounds, salts and complexes can be used as insulin simulators in the treatment of diabetes and for the treatment of hypertension and obesity. Known insulin-simulating vanadium salts are sodium orthovanadate ($Na_3VO_4$), vanadyl sulphate ($VOSO_4.(H_2O)_x$) and other reaction products of vanadate and peroxide.

Numerous vanadium compounds, salts and complexes which are effective in the treatment of diabetes, hypertension and obesity are described in U.S. Pat. No. 5,520,967. The compounds, salts and complexes concerned here are vanadium complexes of monoprotic bidentate ligands, which are capable of chelating vanadium to a five- or six-membered, unsaturated vanadium-containing ring, said ring containing at least two other hetero-atoms in addition to vanadium and said ring containing vanadium-coordinating oxygen and nitrogen hetero-atoms if the ring is a six-membered ring. Examples of compounds which form a five-membered ring as ligand are $\alpha$-amino acids, hydroxamates, thiohydroxamates, $\alpha$-hydroxypyridinones or $\alpha$-hydroxypyrones, such as maltol or kojic acid. Examples of compounds which form a six-membered ring as ligand are substituted or unsubstituted 2-oxazolin-2-ylphenols and 2-thiazolin-2-ylphenols.

It has now been found that known vanadium compounds, salts and complexes prevent indirect or secondary injury of healthy tissue, wherein said indirect or secondary injury is induced by direct or primary injury of tissue mainly surrounding the healthy tissue which is caused by a trauma. The prior art discussed above, however, does neither suggest nor teach the use of vanadium compounds to prevent indirect or secondary injury of healthy issue which is induced by direct or primary injury of tissue mainly surrounding the healthy tissue which is a result of a traumatic event. The prior art suggests a link between apoptosis of some tissues but provides no in vitro data or in vivo data of inhibition of apoptosis by any treatment. It also provides no in vitro or in vivo data on treatment of indirect injury of any kind. Neither is any data provided illustrating apoptosis is responsible for indirect injury. Although the applicant does not wish to be bound by theory, it is suggested that this indirect or secondary injury of healthy tissue may be caused by apoptosis, said apoptosis being induced by directly or primarily injured cells mainly surrounding said healthy tissue. The present invention therefore relates to the use of a physiologically acceptable vanadium compound as active component in the preparation of a pharmaceutical composition for the of secondary injury of tissue, said prophylactic treatment secondary injury being induced by primary injury of mainly surrounding tissue and being the result of a traumatic event.

In general, regeneration of proliferative tissue takes place by enhanced cell proliferation when said proliferative tissue has been damaged by degeneration. On the other hand, regeneration of damaged non-proliferative tissue is obviously not possible as such tissue is not capable of proliferation.

Regeneration takes place entirely independently of the cause of the damage, whether said cause is, for example, ischacmia (infarction) or trauma. With damage as a consequence of ischaemia or trauma, indirect or secondary damage occurs in addition to direct damage or primary damage. The indirect or secondary damage occurs in tissue mainly surrounding the tissue already injured by the direct or primary damage, said indirect or secondary damage possibly being the result of a process involving apoptosis of cells of the tissue damaged by direct or primary injury. In many cases this indirect damage is greater than the direct damage. Although in proliferative tissue proliferation can be stimulated thereby inducing regeneration of said tissue, non-proliferative tissue can obviously not proliferate and the damaging of non-proliferative tissue is an irreversible process. It is therefore essential for the patient that the effects of indirect or secondary are restricted to a minimum or, preferably, are prevented.

Unexpectedly, very good results are obtained when the vanadium compound is administered via a single dose, preferably intravenously, e.g. via a bolus injection, or orally. The prior art mentioning treatment with vanadium of any kind has been silent with regard to any advantage of such administration. The single dose in addition reduces the burden on the patient as prolonged administration which may be detrimental to the physical state of the patient or which may give rise to side effects is not required. According to the invention the vanadium compound is particularly administered intravenously.

Preferably, the vanadium compound is administered prior to the traumatic event where possible or immediately or shortly after said event. If the event involves an operation e.g. the vanadium compound can be administered at a suitable moment prior to said operation. The vanadium compound can be administered up to two weeks after the event, preferably within 24 h and in particular within 2 h of the event is suitable. As soon as possible after the traumatic event treatment is preferably carried out. The exact timing will depend on the circumstance of the patient and will be assessed by the attending physician.

If the traumatic event is an operation, the operation itself would cause direct or primary injury to tissue thereby causing indirect or secondary injury to mainly surrounding tissue under normal circumstances. According to the invention, said indirect or secondary injury can be prevented by administering a single dose of a suitable amount of the vanadium compound to the patient before the operation is conducted, i.e. normally within a few hours prior to the operation. Alternatively, if the traumatic event is ischaemia followed by reperfusion, the indirect or secondary injury is prevented to administer in a single dose a suitable amount of the vanadium compound as fast as possible after the event took place. However, even after 24 h such an administration is capable of preventing said indirect or secondary injury. Moreover, if the traumatic event is a hum, prevention of indirect or secondary injury is achieved even if the vanadium compound is administered four to five days after the burn occurred. The vanadium compound can therefore be administered one week after the traumatic event, preferably within said period e.g. within 24 h and in particular 2 h after such events.

According to the invention the vanadium compound may also be added to media for tissue or organ transplantations or to media for transport of tissue and organs to be transplanted thereby preventing cell death of said tissue or organs due to secondary injury of the implanted or transplanted tissue or organ by anoxia/hypoxia or deprivation of growth factors. Also in such cases addition is preferable as soon as possible after removal of the donor organ or tissue.

According to a preferred embodiment of the present invention the tissue to be protected from indirect or secondary injury is non-proliferative tissue, in particular heart, kidney, liver, nervous or other differentiated tissue. As elucidated in the introductory part of the description directly injured non-proliferative tissue is excluded from treatment according to the invention. The non-proliferative tissue to be treated according to the invention is in particular myocardial or heart tissue. The traumatic event when treating such tissue is in particular reperfusion after ischaemia. Reperfusion damage occurs in addition to direct or primary damage caused by ischaemia and the indirect or secondary injury is very often greater than the direct or primary injury with the ratio of these injuries estimated as being 70:30. Consequently, the prevention of the secondary injury, e.g. caused by reperfusion after ischaemia, is of significant interest for a patient suffering from primary injury, e.g. caused by ischaemia.

Another important example of traumatic events to be treated according to the invention are burns on epidermal tissue. Burns, in particular second and third degree burns are known to damage structures present in the dermis such as the deep vascular plexus, the hair-adnexes (sebaceous glands) and sweat glands. The vanadium compounds, salts and complexes when administered intravenously in a single dose are capable to protect these structures from indirect or secondary injury. These structures are non-proliferative and epidermal tissue as such is proliferative tissue. Furthermore, contractions of scars are reduced to a minimum. Interestingly, major differences were observed between wound healing effects which, on the one hand, can be influenced by growth factors or growth factor simulating agents, and, on the other, the prevention of indirect or secondary injury induced by these burns which cannot be influenced by growth factors or growth factor simulating agents only. This reiterates the comments made in the introductory part regarding prior art disclosures suggesting use of vanadium for treatment associated with stimulating growth factor activity and shows the difference between or our invention and said prior art.

Treatments of burns according to the state of the art can result in faster healing, however none are described as or arc in fact capable of preventing indirect injury of structures such as the deep vascular plexus, the hair-adnexes (sebaceous glands) and sweat glands and cannot prevent severe contractions of scars. The invention, however, provides a composition which is very efficacious for preventing such indirect or secondary injury.

According to the invention the vanadium compounds are preferably administered intravenously or orally. Topical treatment of burns with the vanadium compounds) salt or complexes does not prevent secondary injury, probably due to the impermeability of the burned tissue for vanadium compounds.

Suitable vanadium salts are in principle all physiologically acceptable vanadium salts. Examples of such salts, which, for example, are already being used as an insulin replacement for diabetes patients, arc sodium orthovanadate and vanadyl sulphate. Vanadium complexes that can be used are known, physiologically acceptable complexes. Said complexes comprise both vanadyl and vanadium complexes. Complex-forming units that can be used arc, for example, maltol and kojic acid. According to the invention maltol, resulting in bis(maltolato)oxovanadium(IV) or the corresponding bis(maltolato)oxovanadate salt, is preferred. Both the vanadium and vanadyl salts and complexes mentioned above and other suitable vanadium and vanadyl salts and complexes are described in U.S. Pat. No. 5,583,242 and U.S. Pat. No. 5,620,967. In principle all salts and complexes mentioned in the said patents can be used.

According to the invention the vanadium compound, salt or complex is preferably an organovanadium compound, in particular bis(maltolato)oxovanadium(IV) or the corresponding bis(maltolato)oxovanadate salt.

EXAMPLE 1

Area at risk (AR) and infarcted area (IA) were determined in hearts of phenobarbital anaesthetized rats after 60 minutes coronary artery occlusion (CAO) and 180 minutes of reperfusion. At normothennia (36.5–37.5 C body temperature), the LA/AR ratio was found to be 69+2% (mean+standard error margin, n=6) in control rats and 45+3% in rats (n=6, P<0.001) pretreated with 3.3 mg/kg bodyweight (i.v. bolus in 10 minutes) bis(maltolato)oxovanadiurnQV) 25 minutes prior to GAO. The mean AR expressed as percentage of the left ventricle was not different between the control and the experimental group (42+2% and 42+3%, respectively). This experiment demonstrates that the control group suffered more from indirect or secondary injury than the experimental group (IA represents both direct and indirect injury and the proportion of direct injury will be equal for both groups) and that bis(maltolato)oxovanadium(IV) prevents indirect injury of the myocardial tissue to a large extent (cf. FIGS. 1 and 2).

EXAMPLE 2

The Yorkshire pig has been chosen as the experimental animal because of all animal species this domestic pig seems to be the one with morphological and functional skin characteristics nearest to human skin and so best fulfils the requirements of a model for human skin. In basic architecture it resembles human skin in the relative thickness of the epidermis and dermis, the presence of epidermal ridges, a distinct dermal papillary layer and a deep layer of subdermal fat. Compared to human the elastic fibre content of porcine dermis is relatively low, but higher than in any other species. Comparison of human and porcine epidermis and its appendages also suggests common traits. Studies on the proliferation rate of porcine epidermis show parallels with those of humans. The keratinous proteins are similar. Unlike the skin of rodents, the follicular pattern in pigs and humans is relatively sparse and arranged as single hairs or in groups of two or three follicles. Pigs do not sweat. The regulation of body temperature by the skin is more evident in humans than in the pig. In the skin of the pig no eccrine glands are found. It does have apocrine glands, but their role in thermoregulation remains debatable. The vascular anatomy of pig skin consists of a three layered network; lower, mid-dermal and sub epidermal. The size, orientation and distribution of the vessels are strikingly similar to human skin, but it does differ from humans in that the sub epidermal network is less dense. The vascularisation of the lower region of the follicle corresponds to that in humans. The healing of deep dermal burns, which depends on this phenomenon, might also be analogous. Studies on the thermal properties of porcine skin as a function of depth have been performed by measuring the tissue water content. With the use of a mathematical model the heat capacity and thermal conductivity could be calculated and results for pig skin were found to be consistent with those for human skin.

The speed of epithelialization in pigs is dependent on several factors. In full thickness wounds the epithelialization starts only from the wound margins.

In split-thickness wounds, each viable hair follicle is an islet for the reepithelialization. In split-thickness wounds of 2.2×2.2 cm, and 0.04 cm thick, in Yucatan mini pig of six months old it takes about 96 hours before complete re-epithelialization. The SD of the mean degree of epithelialization is ±10%. This shows the inter individual variability. The speed of epithelialization is depending on the age, and is considerable faster in pigs weighting 7 kg in comparison of those weighting 40 kg.

There were no differences in the progression of the epithelialization in the center of the wound in comparison with the wound margin in split-thickness wounds.

Protocol 1a: Twelve identical deep burn wounds were inflicted in each animal. The animal model used is developed in the Burn Research Institute (Beverwijk, The Netherlands) and is a standard for all of the experimental burn wound research. The model is also accepted by the animal experimental commission of the University of Amsterdam.

Protocol 1b: Six biopsies of 6 mm of the burned area were taken from each big and transferred to a non-burned area. Six biopsies of 6 mm of the non-burned area were be taken from each pig and transferred to a burned area. (Determination of the indirect injury) Animals: pig, Yorkshire White, female, +/−30 kg.

In this study we observed that structures present in the dermis such as the deep vascular plexus, the hair-adnexes (sebaceous glands) and sweat glands were protected after bis(maltolato)oxovanadium(TV) was administered intravenously in a single dose. Also contractions of scars were considerably reduced and faster healing was observed.

What is claimed is:

1. A method of prophylactic treatment of secondary injury of humans, said secondary injury being induced by primary injury of mainly surrounding tissue and being the result of a traumatic event, comprising: intravenously administering to a patient in need of such treatment, at least one dose of a physiologically acceptable vanadium compound as an active component of a pharmaceutical composition, wherein the traumatic event is a second or third degree burn.

2. The method according to claim 1, wherein the tissue comprises a deep vascular plexus, hair-adnexes and/or sweat glands.

3. The method according to claim 1, wherein the vanadium compound is an organovanadium compound.

4. The method according to claimed 3, wherein the vanadium compound is bis(maltolato)oxovanadium(IV) or the corresponding bis(maltolato)oxovanadate salt.

* * * * *